(12) United States Patent
Huang et al.

(10) Patent No.: US 11,957,717 B2
(45) Date of Patent: Apr. 16, 2024

(54) ANTI-HUMAN MSLN ANTIBODY AND MSLN-TARGETING IMMUNE EFFECTOR CELL

(71) Applicant: HRAIN BIOTECHNOLOGY CO., LTD., Shanghai (CN)

(72) Inventors: Fei Huang, Shanghai (CN); Tao Peng, Shanghai (CN); Xuemei Zou, Shanghai (CN); Pinglei Liu, Shanghai (CN); Dachun Liu, Shanghai (CN); Hui Huang, Shanghai (CN)

(73) Assignee: HRAIN BIOTECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 18/005,827

(22) PCT Filed: Apr. 9, 2021

(86) PCT No.: PCT/CN2021/086067
§ 371 (c)(1),
(2) Date: Jan. 17, 2023

(87) PCT Pub. No.: WO2022/012097
PCT Pub. Date: Jan. 20, 2022

(65) Prior Publication Data
US 2023/0241104 A1  Aug. 3, 2023

(30) Foreign Application Priority Data

Jul. 16, 2020 (CN) .......................... 202010683324.5

(51) Int. Cl.
*A61K 35/17* (2015.01)
*A61K 39/00* (2006.01)
*A61P 35/00* (2006.01)
*C07K 14/725* (2006.01)
*C07K 16/30* (2006.01)
*C12N 5/0783* (2010.01)

(52) U.S. Cl.
CPC .............. *A61K 35/17* (2013.01); *A61P 35/00* (2018.01); *C07K 14/7051* (2013.01); *C07K 16/30* (2013.01); *C12N 5/0636* (2013.01); *A61K 2039/505* (2013.01)

(58) Field of Classification Search
CPC ... A61K 35/17; A61K 2039/505; A61P 35/00; C07K 14/7051; C07K 16/30; C12N 5/0636
See application file for complete search history.

(56) References Cited

FOREIGN PATENT DOCUMENTS

| CN | 109111528 A | 1/2019 |
| CN | 110251666 A | 9/2019 |
| CN | 110507824 A | 11/2019 |
| CN | 110746508 A | 2/2020 |
| CN | 111560072 A | 8/2020 |
| WO | 2020011970 A1 | 1/2020 |

OTHER PUBLICATIONS

International Search Report and Written Opinion issued in PCT/CN2021/086067, dated Jul. 19, 2021, 16 pages provided, with English translation.
Zhang et al., "Modified CAR T cells targeting membrane-proximal epitope of mesothelin enhances the antitumor function against large solid tumor", Cell Death & Disease, 10, 476, Published: Jun. 17, 2019; Cited in Search Report issued in corresponding Chinese Application (12 pages).
Jiang Lv et al., "Mesothelin as a biomarker for targeted therapy", Biomark Res. Aug. 23, 2019;7:18. doi: 10.1186/s40364-019-0169-8. PMID: 31463062; PMCID: PMC6708176. Cited in Search Report issued in corresponding Chinese Application (18 pages).
Jiang et al., "Advances in Research on Mesothelin Targeting Therapeutic Biologics", China Academic Journal Electronic Publishing House, Progress in Pharmaceutical Sciences, 2019, 43 (12) pp. 922-934, with partial translation. Cited in Search Report issued in corresponding Chinese Application.

*Primary Examiner* — Amy E Juedes
*Assistant Examiner* — Brian Hartnett
(74) *Attorney, Agent, or Firm* — HAMRE, SCHUMANN, MUELLER & LARSON, P.C.

(57) ABSTRACT

The present invention provides an anti-human MSLN-specific antibody and an MSLN-targeting immune effector cell. Also provided is an MSLN-targeting chimeric antigen receptor modified T-cell prepared using the antibody and a use thereof.

18 Claims, 8 Drawing Sheets
Specification includes a Sequence Listing.

ANTI-HUMAN MSLN ANTIBODY AND MSLN-TARGETING IMMUNE EFFECTOR CELL

TECHNICAL FIELD

The present invention belongs to the field of tumor immunotherapy or tumor diagnosis. In particular, the present invention relates to an anti-human MSLN antibody and an MSLN-targeting immune effector cell.

BACKGROUND

Mesothelin (MSLN) is a cell surface glycoprotein, the expression of which is normally limited to mesothelial cells (of the peritoneum, pericardium and pleural cavity), and however, is highly expressed in a variety of tumor types, including ovarian cancer, mesothelioma, non-small cell lung cancer, lung adenocarcinoma, fallopian tube cancer, head and neck cancer, cervical cancer and pancreatic cancer. More and more preclinical and clinical studies have shown that the abnormal expression of MSLN plays an important role in the proliferation, invasion, metastasis, anti-apoptosis and other characteristics of tumor cells. Accordingly, clinical studies have also shown that the expression of MSLN is correlated with tumor load, tumor severity and survival rate. These studies indicate that MSLN can be used as a target for tumor-specific antibody therapy.

Chimeric Antigen Receptor-T (CAR-T) cells are a new immunotherapy method targeting tumor-specific cell surface antigens. Antibodies targeting MSLN or other targeted therapies have been reported. Among them, the American Society of Clinical Oncology (ASCO) presented a clinical trial conducted by the University of Pennsylvania at its 2015 annual meeting. In this trial, the MSLN-targeting CAR-T therapy was firstly and successfully used to treat solid tumors, in which 6 patients with refractory pancreatic cancer received treatment. Among them, 4 patients progressed and 2 patients were in stable condition (during 3.7 months and 5.3 months), including one patient without metastatic lesions. At the same time, the infusion of MSLN CAR-T cells did not cause acute side effects. Therefore, MSLN CAR-T cell immunotherapy will provide a new therapeutic method for MSLN positive tumors.

In view of this, an MSLN-specific antibody and an MSLN-targeting immune effector cell are urgently needed in the art.

SUMMARY OF THE INVENTION

The purpose of the present invention is to provide an MSLN-specific antibody and an MSLN-targeting immune effector cell.

In a specific embodiment, the antibody is selected from any one of the following:
(1) an antibody, comprising HCDR1 as shown in SEQ ID NO: 1, HCDR2 as shown in SEQ ID NO: 2, HCDR3 as shown in SEQ ID NO: 3, LCDR1 as shown in SEQ ID NO: 4, LCDR2 as shown in SEQ ID NO: 5, and LCDR3 as shown in SEQ ID NO: 6;
(2) an antibody, comprising HCDR1 as shown in SEQ ID NO: 7, HCDR2 as shown in SEQ ID NO: 8, HCDR3 as shown in SEQ ID NO: 9, LCDR1 as shown in SEQ ID NO: 10, LCDR2 as shown in SEQ ID NO: 11, and LCDR3 as shown in SEQ ID NO: 12;
(3) an antibody, comprising HCDR1 as shown in SEQ ID NO: 13, HCDR2 as shown in SEQ ID NO: 14, HCDR3 as shown in SEQ ID NO: 15, LCDR1 as shown in SEQ ID NO: 16, LCDR2 as shown in SEQ ID NO: 17, and LCDR3 as shown in SEQ ID NO: 18;
(4) an antibody, which is a variant of the antibody in any one of (1)~(3), and has the same or similar activities as the antibody in any of (1)~(3).

In one embodiment, the antibody or antigen binding fragment thereof is mouse-derived, chimeric or humanized. In one embodiment, the antibody or antigen binding fragment thereof is an scFv antibody fragment, a Fab antibody fragment or a complete antibody. In one embodiment, the heavy chain of the antibody or antigen binding fragment thereof is the heavy chain of IgG, comprising IgG1, IgG2, IgG3 and IgG4, especially IgG1. In one embodiment, the light chain of the antibody or antigen binding fragment thereof is kappa (κ) light chain or lambda (λ) light chain, especially kappa light chain. In one embodiment, the antibody or antigen binding fragment thereof specifically binds to the extracellular domain of human MSLN.

In one aspect, the present invention relates to at least one polynucleotide encoding an anti-human MSLN antibody or antigen binding fragment thereof of the present invention. In one aspect, the present invention relates to a vector comprising the polynucleotide of the present invention. In one embodiment, the vector is a cloning vector or an expression vector. In one embodiment, the vector is a plasmid vector. In one aspect, the present invention relates to a host cell comprising the polynucleotide or the vector of the present invention. In one embodiment, the host cell is a prokaryotic cell. In one embodiment, the host cell is an *Escherichia coli* cell. In one embodiment, the host cell is a eukaryotic cell. In one embodiment, the host cell is a Chinese hamster ovary cell. In one aspect, the present invention relates to a method of generating an antibody or antigen binding fragment thereof, which comprises culturing the host cell of the present invention under a condition that the antibody or antigen binding fragment thereof is expressed. In one aspect, the present invention relates to a pharmaceutical composition comprising the antibody or antigen binding fragment thereof of the present invention and one or more pharmaceutically acceptable carriers.

In one aspect, the present invention relates to an anti-human MSLN chimeric antigen receptor, which comprises an extracellular region, a transmembrane region and an intracellular region, wherein the extracellular region comprises an antigen binding region, and the antigen binding region comprises a heavy chain variable domain and a light chain variable domain.

In one embodiment, the antigen binding region is an scFv antibody fragment.

In one embodiment, the extracellular region comprises a hinge region. In one embodiment, the hinge region comprises a human CD8α hinge region. In one embodiment, the human CD8α hinge region has an amino acid sequence as shown in SEQ ID NO: 29. In one embodiment, the transmembrane region comprises a human CD8α transmembrane region. In one embodiment, the human CD8α transmembrane region has an amino acid sequence as shown in SEQ ID NO: 31. In one embodiment, the intracellular region comprises one or more signaling regions. In one embodiment, the intracellular region comprises a human CD3ζ intracellular region. In one embodiment, the human CD3ζ intracellular region has an amino acid sequence as shown in SEQ ID NO: 37. In one embodiment, the intracellular region comprises a human CD28 intracellular region and/or a human 41BB intracellular region. In one embodiment, the human CD28 intracellular region has an amino acid sequence as shown in SEQ ID NO: 33 and/or the human 41BB intracellular region has an amino acid sequence as shown in SEQ ID NO: 35.

In one aspect, the present invention relates to a polypeptide comprising a signal peptide and the chimeric antigen receptor of the present invention. In one embodiment, the signal peptide is an IgKss signal peptide. In one embodiment, the IgKss signal peptide has an amino acid sequence as shown in SEQ ID NO: 27.

In one aspect, the present invention relates to a polynucleotide encoding the chimeric antigen receptor or the polypeptide of the present invention. In one aspect, the present invention relates to a vector comprising the polynucleotide of the present invention. In one embodiment, the vector is a cloning vector or a transfection vector. In one embodiment, the vector is a virus vector. In one aspect, the present invention relates to a modified immune effector cell, which expresses the chimeric antigen receptor or the polypeptide of the present invention, or comprises a polynucleotide encoding the chimeric antigen receptor or the polypeptide of the present invention. In one embodiment, the modified immune effector cell is selected from a T lymphocyte, a NK cell, an immune cell cultured and differentiated from a multipotential stem cell or an embryonic stem cell. In one embodiment, the modified immune effector cell is a T lymphocyte. In one aspect, the present invention relates to a method of modifying an immune effector cell, which comprises transfecting the immune effector cell with the vector of the present invention. In one embodiment, the modified immune effector cell is selected from a T lymphocyte, a NK cell, a immune cell cultured and differentiated from a multipotential stem cell or an embryonic stem cell. In one embodiment, the modified immune effector cell is a T lymphocyte.

In one aspect, the present invention relates to use of the antibody or antigen binding fragment thereof, the chimeric antigen receptor, the polypeptide, the polynucleotide, the vector, or the modified immune effector cell of the present invention in the manufacture of a medicament for use in treating a cancer. In one aspect, the present invention relates to use of the antibody or antigen binding fragment thereof, the chimeric antigen receptor, the polypeptide, the polynucleotide, the vector, or the modified immune effector cell of the present invention in the manufacture of a medicament for use in stimulating immune function in a patient with a cancer. In one aspect, the present invention relates to a method of treating cancer, which comprises administering the antibody or antigen binding fragment thereof, the chimeric antigen receptor, the polypeptide, the polynucleotide, the vector, or the modified immune effector cell of the present invention to a patient with a cancer. In one aspect, the present invention relates to a method of stimulating immune function in a patient with a cancer, which comprises administering the antibody or antigen binding fragment thereof, the chimeric antigen receptor, the polypeptide, the polynucleotide, the vector, or the modified immune effector cell of the present invention to the patient. In one embodiment, the cancer is an MSLN positive cancer. In one embodiment, the cancer is a mesothelioma, pancreatic cancer or ovarian cancer. In one embodiment, the immune function is IFN-γ secretion and/or CD107a expression.

It should be understood that within the scope of the present invention, the various technical features of the present invention above and the various technical features specifically described hereinafter (as in the embodiments) may be combined with each other to constitute a new or preferred technical solution. Due to space limitations, it is not repeated here.

MODES FOR CARRYING OUT THE INVENTION

Figure 1:
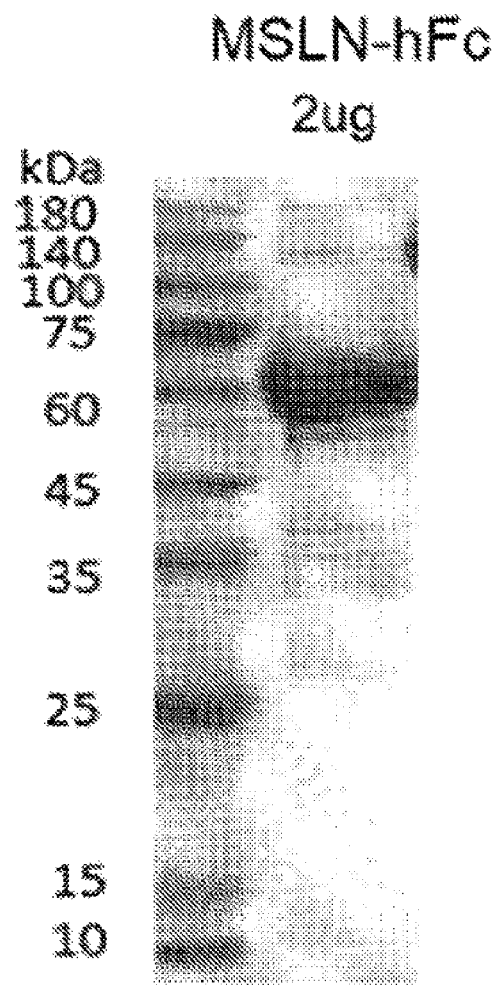
FIG. 1 shows the SDS electrophoretogram (reduction conditions) of the recombinant MSLN-huIgG1 Fc fusion protein.

Unless otherwise defined, the technical and scientific terms used herein have the same meanings as those commonly understood by those skilled in the art to which the present invention belongs.

Unless otherwise stated, conventional techniques of molecular biology, microbiology, cell biology, biochemistry and immunology are adopted for the implementation of the present invention. These techniques are within the technical scope of the present field and are fully described in the literatures.

It should be understood that the embodiments of "comprising" described herein include those of "consisting of" and/or "substantially consisting of".

Anti-MSLN Antibody

One aspect of the present invention provides an anti-MSLN antibody specifically binding to MSLN (such as human MSLN, especially the extracellular domain of human MSLN). In some embodiments, the anti-MSLN antibody of the present invention is a monoclonal antibody.

In some embodiments, the anti-MSLN antibody of the present invention is a full-length antibody. The terms "full-length antibody", "complete antibody" and "whole antibody" are used interchangeably herein, and refer to an antibody in basically complete form compared with an antibody fragment. The terms "antibody" and "immunoglobulin" are used interchangeably herein. The basic 4-chain antibody unit is a heterotetrameric glycoprotein consisting of two identical light (L) chains and two identical heavy (H) chains. L-chains from any vertebrate species can be classified into two distinct types according to the amino acid sequences of their constant regions, called kappa (κ) and lambda (λ). Antibodies can be classified into five different classes according to the amino acid sequences of their heavy chain constant regions: IgA, IgD, IgE, IgG and IgM, which have heavy chains called α, δ, ε, γ and μ, respectively. IgG and IgA can be further divided into subclasses, such as IgG1, IgG2 (including IgG2A and IgG2B), IgG3, IgG4, IgA1 and IgA2. In terms of IgG, the 4-chain unit is usually about 150,000 Daltons. Each H-chain has a variable domain (VH) at the N-terminus, followed by three constant domains (CH) of each γ-chain. Each L-chain has a variable domain (VL) at the N-terminus, followed by a constant domain (CL) at the other end.

In some embodiments, the anti-MSLN antibody of the present invention is an IgG antibody, especially IgG1 antibody. In some embodiments, the anti-MSLN antibody of the present invention is a kappa antibody.

In some embodiments, the anti-MSLN antibody of the present invention is an antibody fragment. The term "antibody fragment" comprises a portion of a complete antibody, preferably an antigen binding region and/or a variable region of the complete antibody. Examples of the antibody fragment include Fab, Fab', Fab'-SH, F(ab')2, Fv, and scFv fragments; diabody; linear antibody; single chain antibody; and multi-specific antibody formed from antibody fragments. The term "scFv" is an antibody fragment comprising VH and VL domains connected into a single polypeptide chain. Preferably, the scFv also comprises a polypeptide linker between VH and VL domains. The term "Fab" consists of the entire L-chain and the variable domain (VH) and the first constant domain (CH1) of the H-chain.

In some embodiments, the anti-MSLN antibody of the present invention is an antigen binding fragment, which comprises a heavy chain variable domain and a light chain variable domain of the parent antibody, such as scFv or Fab. Antibody fragments can be prepared by a variety of techniques, including but not limited to proteolytic digestion of complete antibodies and production by recombinant host cells.

In some embodiments, the anti-MSLN antibody of the present invention is mouse-derived, chimeric or humanized.

In the "chimeric" antibody, a part of the heavy chain and/or light chain is the same or homologous with the corresponding sequence in an antibody from a specific species or belonging to a specific antibody class or subclass, while the rest of the heavy chain and/or light chain is the same or homologous with the corresponding sequence in an antibody from another species or belonging to another antibody class or subclass, as long as they show the required biological activities. In some embodiments, the chimeric antibody of the present invention comprises a murine variable region and a human constant region.

The "humanized" form of a non-human (e.g., murine) antibody is a chimeric antibody comprising the smallest sequence from the non-human antibody. In some embodiments, the humanized antibody is a human antibody (receptor antibody) in which CDR (or HVR) residues of the receptor antibody are replaced by CDR (or HVR) residues of a non-human species, such as mice, rats, rabbits or non-human primates (donor antibody) with the desired specificity, affinity and/or ability. In some cases, frame ("FR") residues of the human antibody are replaced by corresponding non-human residues. In addition, the humanized antibody may comprise residues that are not present in either the receptor antibody or the donor antibody. These modifications can be performed to further improve antibody performance, such as binding affinity.

In some embodiments, the present invention covers antibodies that bind to the same MSLN epitope as any one of the anti-MSLN antibodies described herein. In some embodiments, the present invention covers antibodies that competitively bind MSLN with any one of the anti-MSLN antibodies described herein. In some embodiments, competitive assays may be used to identify the antibodies that bind to the same MSLN epitope as any one of the anti-MSLN antibodies described herein or the antibodies that competitively bind MSLN with any one of the anti-MSLN antibodies described herein. In some embodiments, if one antibody blocks the binding of another antibody to an antigen by 50% or more, it is considered that the two antibodies bind to the same epitope.

One aspect of the present invention provides one or more polynucleotides, which encode the anti-MSLN antibody of the present invention. One aspect of the present invention provides a vector, which comprises the polynucleotide of the present invention. In one embodiment, the vector is a cloning vector or an expression vector, especially a plasmid vector. One aspect of the present invention provides a host cell, which comprises the polynucleotide or the vector of the present invention. In one embodiment, the host cell is a prokaryotic cell, especially an *Escherichia coli* cell. In another embodiment, the host cell is a eukaryotic cell, especially a Chinese hamster ovary cell. One aspect of the present invention provides a method of generating an anti-MSLN antibody, which comprises culturing the host cell of the present invention under the condition that the antibody is expressed.

Chimeric Antigen Receptor

One aspect of the present invention provides an MSLN-targeting chimeric antigen receptor (CAR). A chimeric antigen receptor is generally composed of extracellular, transmembrane and intracellular regions. The extracellular region comprises an antigen binding region and an optional hinge region. The intracellular region comprises one or more signaling regions, including costimulatory signaling regions. When expressed in cells, a polypeptide of the chimeric antigen receptor can also comprise a signal peptide, especially a membrane localization signal peptide.

When expressed in cells, the polypeptide of the chimeric antigen receptor of the present invention can comprise a signal peptide (also called a signal sequence) at the N-terminus of the polypeptide. In general, a signal peptide is a peptide sequence that enables the polypeptide to target the desired sites in cells. In some embodiments, the signal peptide enables the polypeptide to target the secretory pathway of the cells, and will allow the polypeptide to be integrated and anchored to the lipid bilayer.

In some embodiments, the signal peptide used in the present invention is a membrane localization signal peptide. In some embodiments, the signal peptide used in the present invention is derived from IgK. In some embodiments, the IgKss signal peptide comprises an amino acid sequence of SEQ ID NO: 27. In some embodiments, the IgKss signal peptide is encoded by a nucleic acid sequence of SEQ ID NO: 28.

The chimeric antigen receptor of the present invention comprises an antigen binding region targeting MSLN. The antigen binding region may be univalent or multivalent (e.g., bivalent). The antigen binding region may also be monospecific or multispecific (e.g., bispecific). The bispecificity can be against MSLN and another antigen, or two different epitopes of MSLN.

In some embodiments, the antigen binding region used in the present invention is the anti-MSLN antibody or antigen binding fragment thereof described above, especially in the form of scFv.

Optionally, the chimeric antigen receptor of the present invention comprises a hinge region located between an extracellular antigen binding region and a transmembrane region. The hinge region is an amino acid region that usually exists between two domains of a protein, and allows the flexibility of the protein and the relative motion of the two domains.

The hinge region may be a hinge region or part thereof of a naturally occurring protein. The hinge region of antibodies (such as IgG, IgA, IgM, IgE, or IgD antibodies) can also be used for the chimeric antigen receptor described herein. Non-naturally occurring peptides can also be used as hinge regions of the chimeric antigen receptor described herein. In some embodiments, the hinge region is a peptide linker.

In some embodiments, the hinge region used in the present invention is derived from CD8α. In some embodiments, a CD8α hinge region comprises an amino acid sequence of SEQ ID NO: 29. In some embodiments, the CD8α hinge region is encoded by a nucleic acid sequence of SEQ ID NO: 30.

The chimeric antibody receptor of the present invention comprises a transmembrane region. The transmembrane region can form an α-helix, a complex of more than one α-helix, a β-barrel or any other stable structure that can cross the phospholipid bilayer of cells. The transmembrane region can be of natural or synthetic origin. The transmembrane region can be derived from the α, β or ζ chain of CDR, CD4ε, CD5, CD8α, CD9, CD16, CD22, CD28, CD33, CD37, CD45, CD64, CD80, CD86, CD134, CD137, CD154, or T cell receptor.

In some embodiments, the transmembrane region used in the present invention is derived from CD8α. In some embodiments, a CD8α transmembrane region comprises an amino acid sequence of SEQ ID NO: 31. In some embodiments, the CD8 transmembrane region is encoded by a nucleic acid sequence of SEQ ID NO: 32.

The chimeric antigen receptor of the present invention comprises an intracellular region. The intracellular region comprises one or more signaling regions, including costimulatory signaling regions.

The intracellular signaling region is responsible for the activation of at least one normal effector function of immune effector cells expressing chimeric antigen receptors. For example, the effector function of T cells can be cell lysis activity or helper activity, including cytokine secretion. Although it is usually possible to use the entire intracellular signaling region, in many cases, it is unnecessary to use the entire chain. As far as the truncated part of the intracellular signaling region is concerned, such truncated part can be used to replace the complete chain, as long as it transduces the signals of effector function. Therefore, the intracellular signaling region comprises any truncated form of the intracellular signaling region that is sufficient to transduce the signals of effector function. In some embodiments, the signaling region is derived from CD3z, FcRγ (FCER1G), FcRβ (Fcε Rib), CD3γ, CD3δ, CD3ε, CD5, CD22, CD79a, CD79b, and CD66d.

In some embodiments, the signaling region used in the present invention is derived from CD3z. In some embodiments, a CD3z signaling region comprises an amino acid sequence of SEQ ID NO: 37. In some embodiments, the CD3z signaling region is encoded by a nucleic acid sequence of SEQ ID NO: 38.

In some embodiments, the intracellular region of the chimeric antigen receptor of the present invention also comprises one or more costimulatory signaling regions. In addition to the stimulation of antigen specific signals, many immune effector cells also need co-stimulation to promote cell proliferation, differentiation and survival, as well as to activate the effector function of cells. The "costimulatory signaling region" can be the cytoplasmic part of costimulatory molecules. The term "costimulatory molecule" refers to the associated binding chaperone on immune cells (such as T cells). The associated binding chaperone specifically binds to the costimulatory ligand, so that immune cells can mediate the costimulatory response, such as but not limited to proliferation and survival. The costimulatory signaling region can be derived from the intracellular signaling region of CARD11, CD2, CD7, CD27, CD28, CD30, CD40, CD54, CD83, OX40, CD137, CD134, CD150, CD152, CD223, CD270, PD-L2, PD-L1, CD278, DAP10, LAT, NKD2C, SLP76, TRIM, FcεRIγ, MyD88, and 41BBL; and/or.

In some embodiments, the costimulatory signaling region used in the present invention is derived from CD28 and/or 4-1BB. In some embodiments, a CD28 costimulatory signaling region comprises an amino acid sequence of SEQ ID NO: 33. In some embodiments, the CD28 costimulatory signaling region is encoded by a nucleic acid sequence of SEQ ID NO: 34. In some embodiments, a 4-1BB costimulatory signaling region comprises an amino acid sequence of SEQ ID NO: 35. In some embodiments, the 4-1BB costimulatory signaling region is encoded by a nucleic acid sequence of SEQ ID NO: 36.

In some embodiments, the intracellular region of the chimeric antigen receptor of the present invention comprises the above described CD28 costimulatory signaling region and/or 4-1BB costimulatory signaling region and the above described CD3z signaling region connected in the direction of N-terminus to C-terminus.

One aspect of the present invention provides at least one polynucleotide, which encodes the chimeric antigen receptor or the polypeptide of the present invention. One aspect of the present invention provides a vector, which comprises the polynucleotide of the present invention. In one embodiment, the vector is a cloning vector or an expression vector. In one embodiment, the vector is a virus vector.

One aspect of the present invention provides a vector for cloning and expressing the MSLN-targeting chimeric antigen receptor of the present invention. In some embodiments, the vector is suitable for replication and integration in eukaryotic cells (such as mammalian cells). In some embodiments, the vector is a virus vector. Examples of the virus vector include, but are not limited to, an adenovirus vector, an adeno-associated virus vector, a lentivirus vector, a retroviral vector, a cowpox vector, a herpes simplex virus vector and derivatives thereof.

Many virus-based systems have been developed for gene transfer to mammalian cells. In some embodiments, the lentivirus vector is used. In some embodiments, a self-inactivating lentivirus vector is used. For example, a self-inactivating lentivirus vector carrying the encoding sequence of a chimeric antigen receptor can be packaged using schemes known in the art. The lentivirus vector thus obtained can be used to transduce mammalian cells (such as primary human T cells) in methods known in the art. Vectors derived from lentiviruses are suitable tools to achieve long-term gene transfer, because they allow long-term, stable integration of transgenes and their reproduction in progeny cells. The lentivirus vector also has low immunogenicity and can transduce non-proliferative cells.

Immune Effector Cells Modified by Genetic Engineering

One aspect of the present invention provides a genetically modified cell, which comprises or expresses the MSLN-targeting chimeric antigen receptor of the present invention, such as an immune effector cell.

In some embodiments, the immune effector cell is a T cell, a NK cell, a peripheral blood mononuclear cell (PBMC), a cell (such as an immune cell) cultured and differentiated from a hematopoietic stem cell, a multipotential stem cell, or an embryonic stem cell. In some embodiments, the immune effector cell is autologous. In some embodiments, the immune effector cell is allogeneic.

The "immune effector cell" is an immune cell that can perform immune effector function. In some embodiments, the immune effector cell expresses at least FcγRIII and performs the ADCC effector function. Examples of the immune effector cell mediating ADCC include a peripheral blood mononuclear cell (PBMC), a natural killer (NK) cell, a monocyte, a cytotoxic T cell, a neutrophil, and an eosinophil.

In some embodiments, the immune effector cell is a T cell. In some embodiments, the T cell is CD4+/CD8−, CD4−/CD8+, CD4+/CD8+, CD4−/CD8−, and combinations thereof. In some embodiments, the T cell produces IL-2, IFN, and/or TNF when expressing a chimeric antigen receptor and binding to a target cell. In some embodiments, a CD8+T cell lyses an antigen-specific target cell when expressing the chimeric antigen receptor and binding to the target cell.

A genetically modified immune effector cell is prepared by introducing a chimeric antigen receptor into an immune effector cell (such as a T cell). In some embodiments, the chimeric antigen receptor is introduced into the immune effector cell by transfecting a nucleic acid or a vector comprising a sequence encoding the chimeric antigen receptor. In some embodiments, the chimeric antigen receptor is introduced into the immune effector cell by inserting a protein into the cell membrane and simultaneously allowing the cell to pass through the microfluidic system.

The method of introducing a nucleic acid or a vector into a mammalian cell is known in the art. The vector can be transferred into an immune effector cell by physical, chemical or biological methods. Physical methods of introducing the vector into the immune effector cell include calcium phosphate precipitation, liposome transfection, particle bombardment, microinjection, electroporation, etc. Chemical means for introducing the nucleic acid or the vector into the immune effector cell include a colloidal dispersion system, such as a macromolecular complex, a nanocapsule, a microsphere, a bead, and a lipid-based system (including an oil-in-water emulsion, a micelle, a mixed micelle, and a liposome). An exemplary colloidal system used as an in vitro delivery vehicle is a liposome (such as an artificial membrane vesicle). Biological methods of introducing the nucleic acid or the vector into the immune effector cell include the use of DNA and RNA vectors. Virus vectors have become the most widely used method for inserting genes into mammalian cells, such as human cells.

In some embodiments, the transduced or transfected immune effector cell reproduces ex vivo after the introduction of a nucleic acid or a vector. In some embodiments, the transduced or transfected immune effector cell is further evaluated or screened to select the modified immune effector cell.

Pharmaceutical Composition

One aspect of the present invention provides a pharmaceutical composition comprising one or more antibodies or antigen binding fragments thereof, chimeric antigen receptors or modified immune effector cells of the present invention and one or more pharmaceutically acceptable carriers.

The pharmaceutical composition can be prepared in the form of a lyophilized preparation or an aqueous solution by mixing an active agent with a desired purity with any pharmaceutically acceptable carrier. The pharmaceutically acceptable carrier is non-toxic to the recipient at the dosage and concentration used, and includes buffer, antioxidant, preservative, isotonizing agent, stabilizing agent, surfactant, etc.

For being used in vivo, pharmaceutical compositions must be sterile. The pharmaceutical compositions can be sterilized by filtering them through a sterile membrane filter.

The pharmaceutical composition may comprise more than one active agent required for the specific indication to be treated, preferably active agents with complementary activity that does not adversely affect each other. Alternatively or in addition, the pharmaceutical composition may also comprise a cytotoxic agent, a chemotherapeutic agent, a cytokine, an immunosuppressant or a growth inhibitor. Such molecules are properly associated in an amount effective for the intended purpose.

Advantages of the Present Invention:

1. The present invention provides an MSLN-specific antibody;

2. The present invention provides an MSLN-targeting immune effector cell;

3. The antibody of the present invention can effectively bind MSLN-expressing tumor cells, and the immune effector cell of the present invention shows significant killing ability to MSLN-expressing tumor cells. Therefore, the antibody and immune effector cell of the present invention can be effectively and safely applied to the treatment of MSLN positive tumors, thus laying a material foundation for the treatment of MSLN positive tumors.

The present invention will be further illustrated below with reference to the specific examples. It should be understood that these examples are only to illustrate the present invention, not to limit the scope of the present invention. The experimental methods with no specific conditions described in the following examples are generally performed under the conventional conditions, e.g., the conditions described by Sambrook et al., Molecular Cloning: Laboratory Guide (New York: Cold Spring Harbor Laboratory Press, 1989), or according to the manufacturer's instructions. Unless otherwise stated, the experimental materials and reagents used in the following examples are commercially available.

Example 1: Construction of Expression Vector of a Fusion Protein (MSLN-huIgG1 Fc) Composed of Amino Acid Sequence from Position 296 to Position 580 of Recombinant Human Mesothelin (MSLN) and Human IgG1 Fc Region and Eukaryotic Expression Thereof 1. Synthesis of gene sequence of amino acid sequence from position 296 to 580 of MSLN and construction of expression vector of MSLN-huIgG1 Fc fusion protein The gene sequence of human mesothelin (MSLN) (NCBI accession No. NP_005814.2) from glutamic acid at position 296 to glycine at position 580 was synthesized by chemical synthesis, and the gene sequence encoded an amino acid sequence as shown in SEQ ID NO: 39.

The gene sequence of human IgG1 heavy chain constant region (UniProtKB/Swiss-Prot accession No. POI857.1) from glutamic acid at position 99 to lysine at position 330 was synthesized by chemical synthesis, and the gene sequence encoded an amino acid sequence as shown in SEQ ID NO: 40.

Chemically synthesized upstream primers comprising signal peptide (with an amino acid sequence as shown in SEQ ID NO: 41) gene sequence were used for constructing the expression vector. MSLN gene fragments were spliced with human IgG1 Fc gene fragments through molecular cloning. The splicing product was cloned into pCDNA3.1 (Thermo) with a TaKaRa seamless cloning kit.

2. Expression and purification of recombinant MSLN-huIgG1 Fc fusion protein

After transfection of 293T cells (ATCC) with this expression vector for 5 days, the culture supernatant was collected and the recombinant MSLN-huIgG1 Fc fusion protein was purified with AKTA explorer 100 (GE). Due to glycosylation modification and other reasons, the recombinant MSLN-huIgG1 Fc fusion protein was shown to have a molecular weight of about 65 k Dalton by Coomassie brilliant blue staining after reduced SDS-PAGE electrophoresis, as shown in FIG. 1.

Example 2: Preparation of Anti-Human MSLN Murine Antibody

1. Animal Immunization 2 mg/mL of MSLN-huIgG1 Fc fusion protein was used as antigen and emulsified with equal volume of complete Freund's adjuvant (Sigma-Aldrich), and then ten 6-week-old female Balb/c mice (Shanghai Research Center of the Southern model organisms) were immunized subcutaneously. After the primary immunization, booster immunization was carried out every ten days, with a total of four subcutaneous immunization. During the fifth immunization, spleens of the mice was directly boosted with the MSLN-huIgG1 Fc fusion protein.

2. Detection of Serum Titer

50 μL of blood was collected from the tail vein before each booster immunization, and the cells were removed by centrifugation while the serum was retained. 50 ng/well of the recombinant MSLN-his (ACRO Biosystems) was added into the ELISA microplate for coating overnight at 4° C. Then, the ELISA microplate was washed three times with PBS, and blocked with 200 μL/well of 1% BSA/PBS at 37° C. for 1 hour. Serially diluted mouse serum was added for binding at 37° C. for 1 hour. The ELISA microplate was washed three times with PBST, and 100 μL of 1:5000 diluted HRP-goat anti-mouse IgG (Shanghai Yisheng Bio-Technology Co., Ltd.) was added for binding at 37° C. for 1 hour. After the ELISA microplate was washed three times with PBST, 100 μL/well of TMB substrate solution was added for development at 37° C. for 10 minutes, and then 100 μL/well of ELISA quenching solution was added. Each well was measured by a microplate reader at OD450.

3. Construction of an Immune Library 3.1 Total cDNA Extraction of Mouse Spleen Cells The mice were sacrificed on the fourth day after the booster immunization by a direct intraperitoneal injection of the MSLN-huIgG1 Fc fusion protein, and the spleens were collected. Then, spleen cells were obtained by grinding the whole spleen with a 70 μm cell sieve (BD). After that, the spleen cells were washed with PBS twice, and centrifuged at 1000 g for 10 minutes to collect the purified spleen cells. Total RNA was extracted with Trizol RNA extraction kit.

The first strand cDNA was synthesized using the SuperScript™ IV First-Strand Synthesis System kit with the RNA as a template.

3.2 Amplification of Antibody Gene and Splicing of Light and Heavy Chains

Using the cDNA as a template, the heavy chain variable domain gene was amplified by PCR using the upstream and downstream primers of the heavy chain variable domain (VH-F, VH-R), and the kappa chain variable domain gene was amplified by PCR using the upstream and downstream primers of the light chain variable domain (VK-F, VK-R). In a 50 μL reaction system, 25 μL of phusion master mix (Thermo), 2.5 μL (25 μmol) of upstream primer, 2.5 μL (25 μmol) of downstream primer, 1.5 μL of DMSO, 0.5 μL of cDNA and 18 μL of ddH$_2$O were added, respectively. PCR reaction was carried out according to the following procedures: pre-denaturation at 98° C. for 1 minute, followed by 30 temperature cycles of denaturation at 98° C. for 30 seconds, annealing at 58° C. for 30 seconds and extension at 72° C. for 1 minute, followed by final extension at 72° C. for 10 minutes.

The amplified VH gene and VK gene were recovered using a DNA gel recovery kit. The same amount of VH gene and VK gene were mixed as a template, and the scFv gene was amplified by overlapping PCR using the upstream primer scFv-F and the downstream primer scFv-R. In a 50 μL reaction system, 25 μL of phusion master mix, 2.5 μL (25 μmol) of upstream primer, 2.5 μL (25 μmol) of downstream primer, 1.5 μL of DMSO, 0.5 μL of cDNA and 18 μL of ddH$_2$O were added, respectively. PCR reaction was carried out according to the following procedures: pre-denaturation at 98° C. for 1 minute, followed by 30 temperature cycles of denaturation at 98° C. for 30 seconds, annealing at 58° C. for 30 seconds and extension at 72° C. for 1 minute, followed by final extension at 72° C. for 10 minute.

The amplified scFv gene fragments were recovered using a DNA gel recovery kit.

3.3 Construction of an Immune Library

The scFv gene fragments and pcomb3XTT vector (The Scripps Research Institute, USA) were digested by SfiI DNA endonuclease. In a 50 μL reaction system, 2 μL of SfiI, 5 μL of 10×buffer and 3 μg of DNA were added, respectively, and ddH$_2$O was added to a final volume of 50 μL. After fully mixing, the 50 μL reaction system was incubated at 50° C. for 3 hours.

After enzyme digestion, the scFv gene fragments and pcomb3XTT vector were recovered using a DNA gel recovery kit, and were cyclized with T4 ligase. In a 50 μL reaction system, 1 μL of T4 ligase, 5 μL of 10×buffer, 100 ng of scFv gene and 500 ng of pcomb3XTT vector were added, respectively, and ddH$_2$O was added to a final volume of 50 μL. After fully mixing, the 50 μL reaction system was incubated at 4° C. for 16 hours. A small amount of product was taken out to verify the ligation efficiency by agarose gel electrophoresis.

10 μL of the above ligated and cyclized product was added into the self-made TG1 electroporation-competent cells, and then the electroporation was performed with an electroporator. 10 μL of electroporated bacteria were taken out, diluted reasonably, and streaked onto plates containing ampicillin. The capacity of phage antibody library was measured according to the counts on the plate. The remaining electroporated bacteria were added into a 2×YT medium containing 100 μg/mL of ampicillin and 2% glucose, and cultured in a heating incubator. After culturing, the medium was centrifuged at 4000 G for 10 minutes at 4° C., and proper amount of glycerol was added into the precipitated bacteria for storing at −80° C. as the antibody-strain library. The scFv immune library with the capacity of more than 5E9 was obtained through multiple accumulation of electroporation.

4. Screening and Identification of a Murine Immune Antibody Phage Library 4.1 Biotinylation of the MSLN-huIgG1 Fc Fusion Protein The standard operating procedures provided by EZ-Link Sulfo-NHS-LC-Biotin were used to randomly biotinylate the MSLN-huIgG1 Fc fusion protein. The binding activity of biotinylated MSLN-huIgG1 Fc fusion protein and SS1 chimeric antibody was verified by ELISA.

4.2 Bio-Panning

The MSLN-huIgG1 Fc fusion protein was taken as the target protein, and the above murine immune antibody library was bio-panned to obtain antibodies binding to the MSLN-huIgG1 Fc fusion protein (especially the extracellular domain of MSLN). 1000D of bacteria were taken from the antibody-strain library, then resuscitated and grown to logarithmic phase. After that, M13K07 helper phage was used to rescue the antibody library. After centrifugation, the mixture was resuspended in 2×YT medium containing ampicillin and kanamycin and amplified overnight at 30° C. The phage was precipitated by PEG/NaCl, and the phage precipitate was dissolved in glycerol/PBST to obtain the phage suspension of the immune library. The casein-blocked phage was put into the co-incubation system of casein-blocked biotinylated MSLN-huIgG1 Fc fusion protein and casein-blocked Dynabeads M-270 streptavidin, and the supernatant of phage suspension was collected. Further, the collected phage suspension was put into the co-incubation system of casein-blocked biotinylated MSLN-huIgG1 Fc fusion protein and casein-blocked Dynabeads M-270 streptavidin, and the magnetic beads were washed with PBST to remove phages that could not bind to MLSN-huIgG1 Fc fusion protein. The phage bound with magnetic beads was eluted with 100 mM of triethylamine and neutralized with 1M Tris-HCl (pH=6.4). 10 µl of eluted phage solution was retained for determining the total phage output, and the remaining phage solution was used for infecting TG1 with logarithmic growth. After overnight amplification, it was regarded as the antibody library for the next round of panning. Three rounds of bio-panning were carried out, and the number of phages put into each round was kept constant at 5E+12 with a difference in that the concentration of MSLN-huIgG1 Fc antigen was 100 nM, 10 nM and 1 nM respectively.

4.3 Screening of Clones Specifically Binding to MLSN Extracellular Domain

The antibody library obtained after the third round of bio-panning was diluted and coated on the plate containing ampicillin to obtain the individual colony, and the individual colony was selected and cultured overnight in a deep-well plate. The next day, the deep-well plate was freeze-thawed repeatedly for three times in a −20° C. refrigerator, and the centrifuged supernatant was used for subsequent ELISA reaction. 50 ng of goat anti-human IgG (Fab-specific) was used in the ELISA reaction for overnight coating. After the ELISA microplate was washed three times with PBS, 200 µL/well of 1% BSA/PBS was added for blocking at 37° C. for 1 hour. After the ELISA microplate was washed three times with PBS, 100 µl of centrifuged supernatant was added for incubating at 37° C. for 1 hour. After the ELISA microplate was washed three times with PBS, 100 µl of biotinylated MSLN-huIgG1 Fc fusion protein at 1 ng/µl concentration was added for incubating at 37° C. for 1 hour. After the ELISA microplate was washed three times with PBST, 100 µl of 1:5000 diluted streptavidin-HRP (Thermo) was added for incubating at 37° C. for 15 minutes. After the ELISA microplate was washed three times with PBST, 100 µL/well of TMB substrate solution was added for development at 37° C. for 10 minutes, and then 100 µL/well of ELISA quenching solution was added. The microplate was measured by a microplate reader at OD450 and three specific clones, 1B6, 1B8 and 1C4, were obtained by positive clone screening. Through sequencing analysis, the heavy chain variable region of 1B6 was the amino acid sequence as shown in SEQ ID NO: 42, and the light chain variable region was the amino acid sequence as shown in SEQ ID NO: 43; the heavy chain variable region of 1B8 was the amino acid sequence as shown in SEQ ID NO: 44, and the light chain variable region was the amino acid sequence as shown in SEQ ID NO: 45; the heavy chain variable region of 1C4 was the amino acid sequence as shown in SEQ ID NO: 46, and the light chain variable region was the amino acid sequence as shown in SEQ ID NO: 47.

4.4 Sorting with Dissociation Rate Constant Koff

Figure 2:
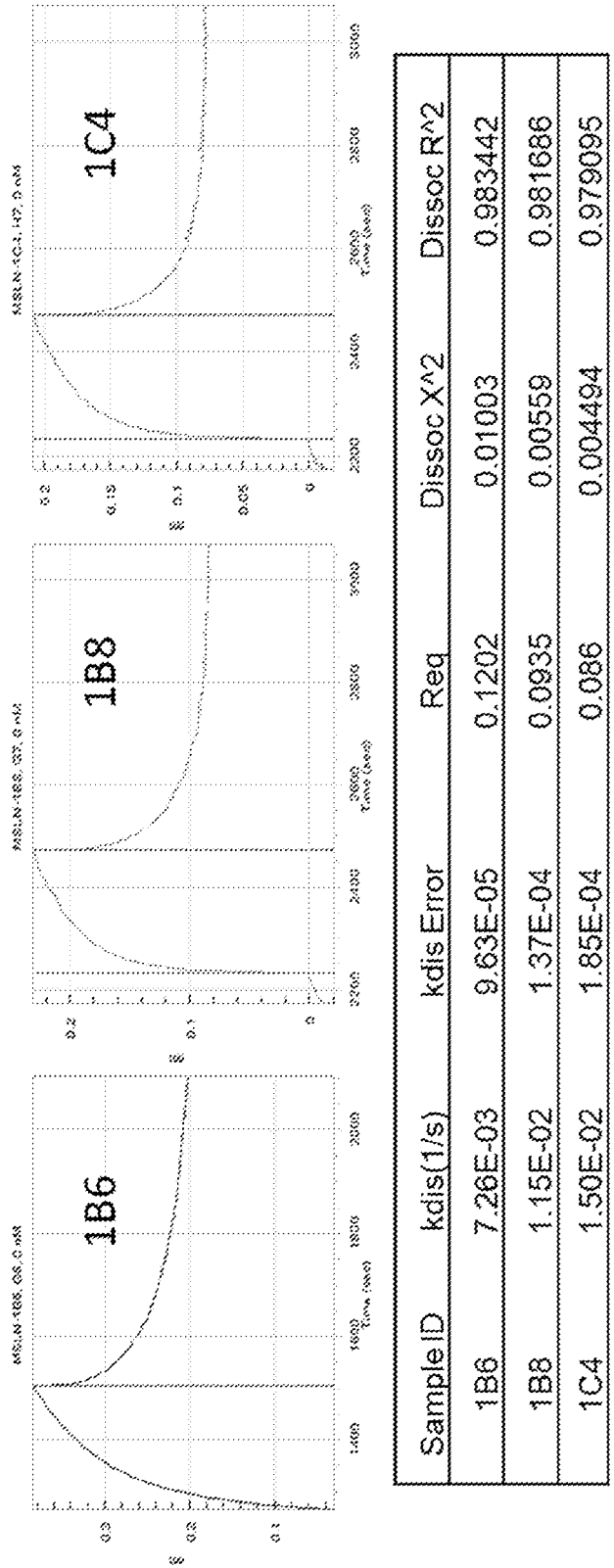
FIG. 2 shows the determination of the dissociation constants of 1B6, 1B8 and 1C4 scFvs with Octet K2 instrument.

The freeze-thaw supernatant of the clones specifically binding to MLSN extracellular segment screened out in the above steps was analyzed by Octet K2 molecular interaction analyzer. The SA probe was solidified with 200 µl of biotinylated MSLN-huIgG1 Fc fusion protein at 100 nM concentration, with a solidification height of 1 nM. The freeze-thaw supernatant was used as the analyte to measure and sort the dissociation constant, and the results were shown in FIG. 2.

Figure 3:
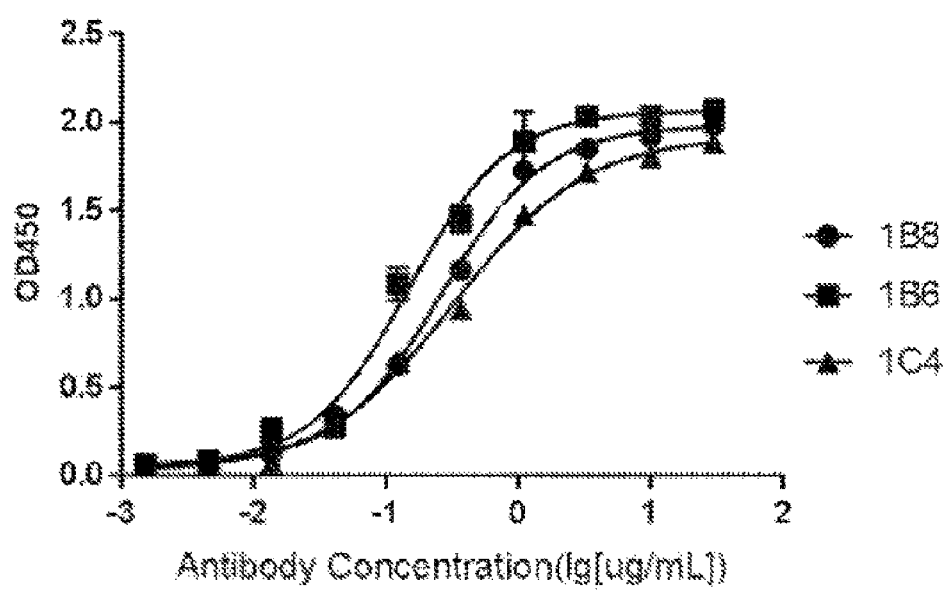
FIG. 3 shows the binding curve of MSLN-huIgG1 Fc with 1B6, 1B8 and 1C4 scFv fragments determined by ELISA.

4.5 Determination of Binding Curves of Recombinant Human MSLN-huIgG1 Fc with 1B6, 1B8 and 1C4 scFv Fragments by ELISA The fusion antibodies of 1B6, 1B8 and 1C4 scFv-Fc were constructed, and they were transiently transfected, expressed and purified in eukaryotic cells. The binding of recombinant human MSLN-huIgG1 Fc with 1B6, 1B8 and 1C4 scFv fragments was detected by enzyme-linked immunosorbent assay (ELISA). ELISA experiment was carried out according to the following procedures: 100 ng/well of the MSLN-huIgG1 Fc fusion protein prepared above was added into a microplate for coating overnight at 4° C. Then, the microplate was washed three times with PBS, and blocked with 200 µL/well of 1% BSA/PBS at 37° C. for 1 hour. After the microplate was washed with 100 µl of PBS, the above three scFv proteins were serially diluted and added into the microplate for binding at 37° C. for 1 hour. The microplate was washed three times with PBST, and 100 µl of 1:5000 diluted HRP-goat anti-human IgG (Fab-specific) was added for binding at 37° C. for 1 hour. After the microplate was washed three times with PBST, 100 µL/well of TMB substrate solution was added for development at 37° C. for 10 minutes, and then 100 µL/well of ELISA quenching solution was added. The microplate was measured by a microplate reader at OD450, and the results were shown in FIG. 3.

Example 3: Construction of Target Cells and Control Cells

1. The Lentivirus Packaging Required for the Construction of Target Cells and Control Cells The luciferase and green fluorescent protein genes which were in series through the internal ribosome entry site (IRES) were synthesized by chemical synthesis. The lentivirus packaging main plasmid (PCCL-LUC-GFP) was constructed by molecular cloning and packaged with lentivirus. The full-length gene of MLSN was constructed into the lentivirus packaging main plasmid (PCCL-MSLN-LUC-GFP) by molecular cloning and packaged with lentivirus.

2. Construction of K562-MSLN-LUC-GFP Target Cells and K562-LUC-GFP Control Cells After transfection of K562 (expressing no MLSN, Cell Bank of Chinese Academy of Sciences) with the above two lentiviruses, K562-MSLN-LUC-GFP target cells with high expression of MSLN protein, luciferase and green fluorescent protein, and K562-LUC-GFP control cells with high expression of luciferase and green fluorescent protein were screened out with green fluorescent protein as markers. At the same time, the expression level of MSLN protein on the surface of K562-MSLN-LUC-GFP target cells was verified by SS1 antibody.

3. Detection of MSLN Expression on OVCAR-3 Cell Surface

The human ovarian cancer cells OVCAR-3 (Cell Bank of Chinese Academy of Sciences), which were considered to express MLSN protein, were also used for follow-up experiments, and the expression level of MSLN protein on the surface of OVCAR-3 was verified by using flow cytometer and MSLN antibody for flow cytometer.

Example 4: Preparation of Lentivirus Stock Solution Containing Anti-Human MSLN Chimeric Antigen Receptor Elements 1. Preparation of Lentivirus Packaging Main Plasmid Containing CAR Elements Using pCCL-c-MNDU3 as the vector, lentivirus plasmids of chimeric antigen receptors expressing 1B6, 1B8, 1C4 and SS1 clones were constructed, including pCCL-c-MNDU3-1B6-28BBz, pCCL-c-MNDU3-1B8-28BBz and pCCL-c-MNDU3-1C4-28BBz. Clones with correctly identified sequence were selected, and bacterial liquid was inoculated into 300 ml of 2YT medium. The bacteria were shaken overnight at 220 rpm and 37° C. The plasmid extraction of a large amount of bacterial liquid was completed according to the instructions of NucleoBondXtra Maxi EF kit.

The 1B6-28BBz sequence was composed of IgKss signal peptide (SEQ ID NO: 28), 1B6 scFv (SEQ ID NO: 20), CD8 hinge (SEQ ID NO: 30), CD8 transmembrane region (SEQ ID NO: 32), CD28 intracellular signaling domain (SEQ ID NO: 34), 4-1BB intracellular signaling domain (SEQ ID NO: 36) and CD3 intracellular segment CD3 (SEQ ID NO: 38), wherein the 1B6 scFv was composed of a heavy chain variable domain (SEQ ID NO: 42) and a light chain variable domain (SEQ ID NO: 43) connected by a linker sequence.

The 1B8-28BBz sequence was composed of IgKss signal peptide (SEQ ID NO: 28), 1B8 scFv (SEQ ID NO: 22), CD8 hinge (SEQ ID NO: 30), CD8 transmembrane region (SEQ ID NO: 32), CD28 intracellular signaling domain (SEQ ID NO: 34), 4-1BB intracellular signaling domain (SEQ ID NO: 36) and CD3 intracellular segment CD3 (SEQ ID NO: 38), wherein the 1B8 scFv was composed of a heavy chain variable domain (SEQ ID NO: 44) and a light chain variable domain (SEQ ID NO: 45) connected by a linker sequence.

The 1C4-28BBz sequence was composed of IgKss signal peptide (SEQ ID NO: 28), 1C4 scFv (SEQ ID NO: 24), CD8 hinge (SEQ ID NO: 30), CD8 transmembrane region (SEQ ID NO: 32), CD28 intracellular signaling domain (SEQ ID NO: 34), 4-1BB intracellular signaling domain (SEQ ID NO: 36) and CD3 intracellular segment CD3 (SEQ ID NO: 38), wherein the 1B8 scFv was composed of a heavy chain variable domain (SEQ ID NO: 46) and a light chain variable domain (SEQ ID NO: 47) connected by a linker sequence.

The SS1-28BBz sequence was composed of IgKss signal peptide (SEQ ID NO: 28), SS1 scFv (SEQ ID NO: 26), CD8 hinge (SEQ ID NO: 30), CD8 transmembrane region (SEQ ID NO: 32), CD28 intracellular signaling domain (SEQ ID NO: 34), 4-1BB intracellular signaling domain (SEQ ID NO: 36) and CD3 intracellular segment CD3 (SEQ ID NO: 38).

2. Packaging of Lentivirus

The lentivirus was packed with cationic polymer PEI, and the process was as follows: PEI and the lentivirus packaging plasmid (lentivirus main plasmid, RRE-SIV, REV, VSVG) were diluted with serum-free DMEM respectively; then PEI/DMEM was added into plasmid/DMEM mixture, and they were mixed well using a vortex mixer and placed at room temperature for 15 minutes; the plasmid-PEI complex was added into the pre-plated 293T cells (Cell Bank of Chinese Academy of Sciences). After 16 hours of transfection, the medium was replaced, and the virus supernatant was collected after 48 h. The virus supernatant was filtered by a 0.45 μm membrane filter and the original solution was retained for subsequent experiments.

Example 5: Preparation of CAR-T Cells and Determination of CAR Positive Rate

1. PBMC Isolation and Activation

The peripheral blood was collected from volunteers, and PBMC was isolated with Ficcol isolation solution (Tianjin Haoyang). The cell density was adjusted to $1 \times 10^6$/mL using X-VIVO (LONZA) medium containing 5% AB serum. The tissue culture-treated 6-well plate was pre-incubated and coated with 1 ml of coating solution containing 50 ng/ml of anti-human CD3 antibody (Beijing Tonglihaiyuan) and 50 ng/ml of CD28 antibody (Beijing Tonglihaiyuan) at 37° C. for 2 h, and the coating solution was removed before use. The cells were inoculated into the 6-well plate coated with antibodies at 1 ml/well, and then 100 IU/ml of IL2 (Beijing Shuanglu) was added for stimulation culture. The virus infection was carried out after 48 hours of stimulation culture.

2. Infection of Virus Stock Solution and Cell Culture

The density of activated T cells was adjusted to $5 \times 10^5$/ml. 1 ml of T cells and 1 ml of virus stock solution were added into a 24-well plate respectively, and 1 μl of polybrene was added into each well. Then the mixture was centrifuged at 32° C. and 2500 rpm for 1.5 h, and the supernatant was discarded. 1 ml of T cell culture medium (containing 100 IU/ml of IL-2) was added into each well. The culture plate was placed in a 5% $CO_2$ incubator at 37° C. for culturing. After 24 hours of infection, the cells were transferred to a 6-well plate, and the density of cells was observed every day. T cell culture medium containing 100 IU/ml of IL-2 was added at the right time to maintain the density of the T cells at about $5 \times 10^5$/ml for cell proliferation.

3. Detection of CAR Positive Rate

Figure 4:
FIG. 4 shows the positive rate of CAR expression in MSLN CAR-T cells.

After 72 hours of virus infection, the CAR positive rate was detected in T lymphocytes infected by lentivirus. For the chimeric antigen receptor groups comprising 1B6, 1B8, 1C4 and SS1 clones and negative control group, $1 \times 10^{\hat{}}6$ cells were taken out respectively and centrifuged to remove the culture medium. After the cells were washed twice with PBS, 100 μl of the cells were resuspended and placed in the sampling tube (BD) for flow cytometry. Biotin-goat anti-mouse IgG F(ab')2 antibody (Thermo) was added according to the recommended proportion and incubated for 20 minutes at four degrees. After the cells were washed twice with PBS, Brilliant Violet 421™ Streptavidin (BioLegend) was added according to the recommended proportion and incubated in darkness for 20 minutes at four degrees. After the cells were washed twice with PBS, 100 μl of the cells were resuspended and tested on the machine. The results of flow cytometry analysis of CAR-T positive rate were shown in FIG. 4.

Example 6: Functional Analysis Based on the Anti-Human MLSN CAR-T Cells

Figure 5:
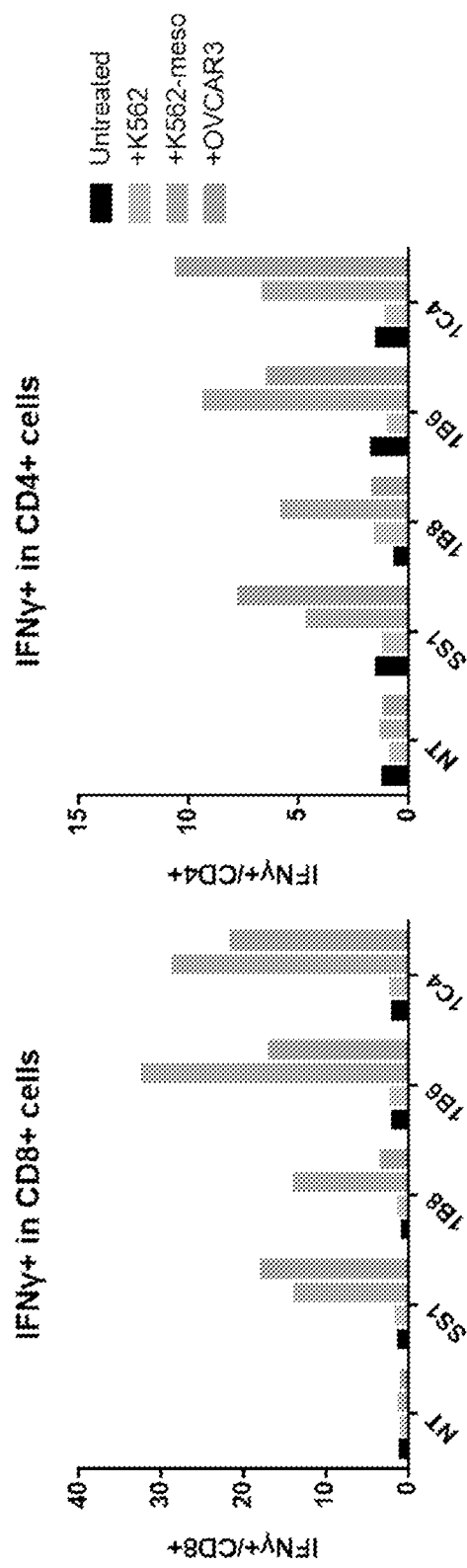
FIG. 5 shows the INFγ secretion of MSLN CAR-T cells.
Figure 6:
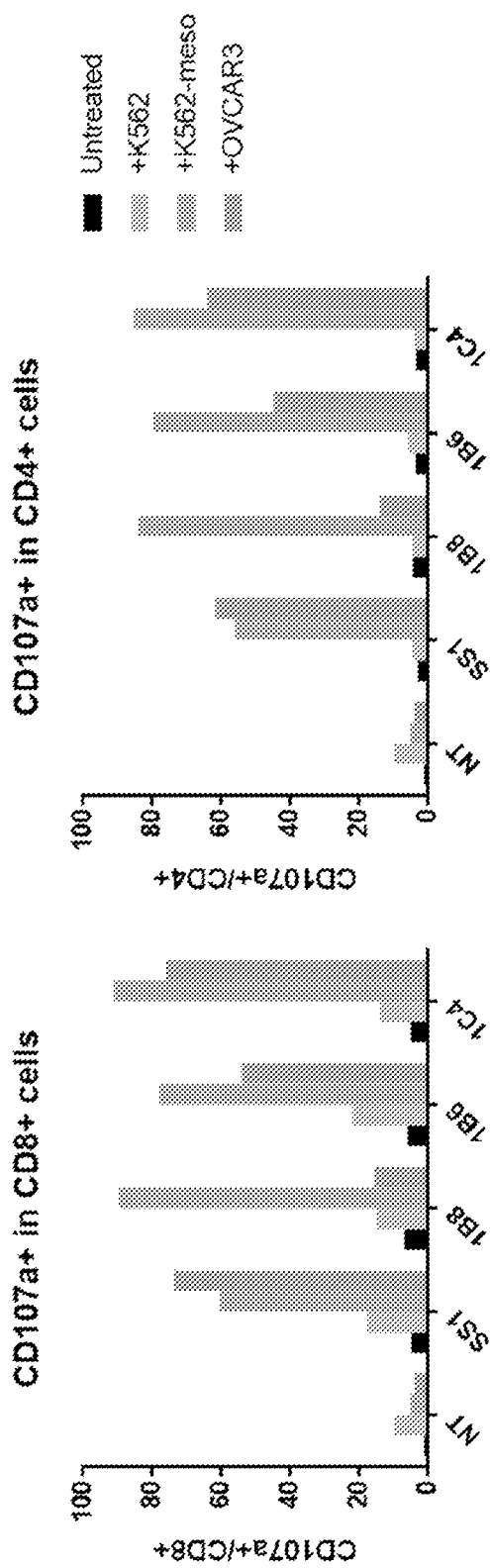
FIG. 6 shows the CD107a expression in MSLN CAR-T cells.

1. Analysis of IFN-γ Secretion and CD107a Expression of the Anti-Human MSLN CAR-T Cells After incubating each type of effector cells (CAR-T cells comprising different antibody clones) with target cells of different groups (OVCAR-3, K562-LUC-GFP and K562-MSLN-LUC-GFP mentioned in Example 5) (the number of the effector cells and the number of the target cells were both $3 \times 10^5$), the IFN-γ expression and CD107a expression thereof were detected by flow cytometry to evaluate the effect function of the CAR-T cells in vitro after being stimulated by the target cells. After the effector cells and target cells were mixed and incubated in a 5% $CO_2$ incubator at 37° C. for 4 hours, the proportion of cells secreting IFN-γ or expressing CD107a to CD4+ cells or CD8+ cells in samples of each group was detected by flow cytometry. The results of flow cytometry analysis of IFN-γ secretion were shown in FIG. 5, and the results of flow cytometry analysis of CD107a expression were shown in FIG. 6.

2. In Vitro Proliferation Experiment of the Anti-Human MSLN CAR-T Cells

Figure 7:
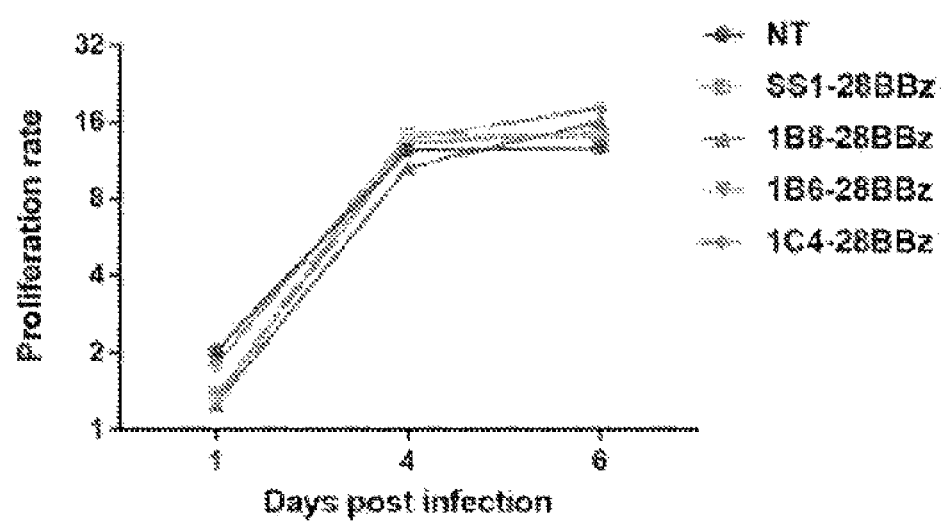
FIG. 7 shows the in vitro proliferation curve of MSLN CAR-T cells.

The densities of anti-human MSLN chimeric antigen receptor-T cells of different groups were adjusted to $3 \times 10^5$/ml, and the cells were maintained with 100 IU/ml of IL-2 in T75 flasks, which were cultured in a 5% $CO_2$ incubator at 37° C. On the fourth day and the sixth day, a cell counter was used to count the number of cells and the cell proliferation rate was calculated. The specific analysis results were shown in FIG. 7.

3. Cytotoxicity Test of the Anti-Human MSLN CAR-T Cells

Figure 8:
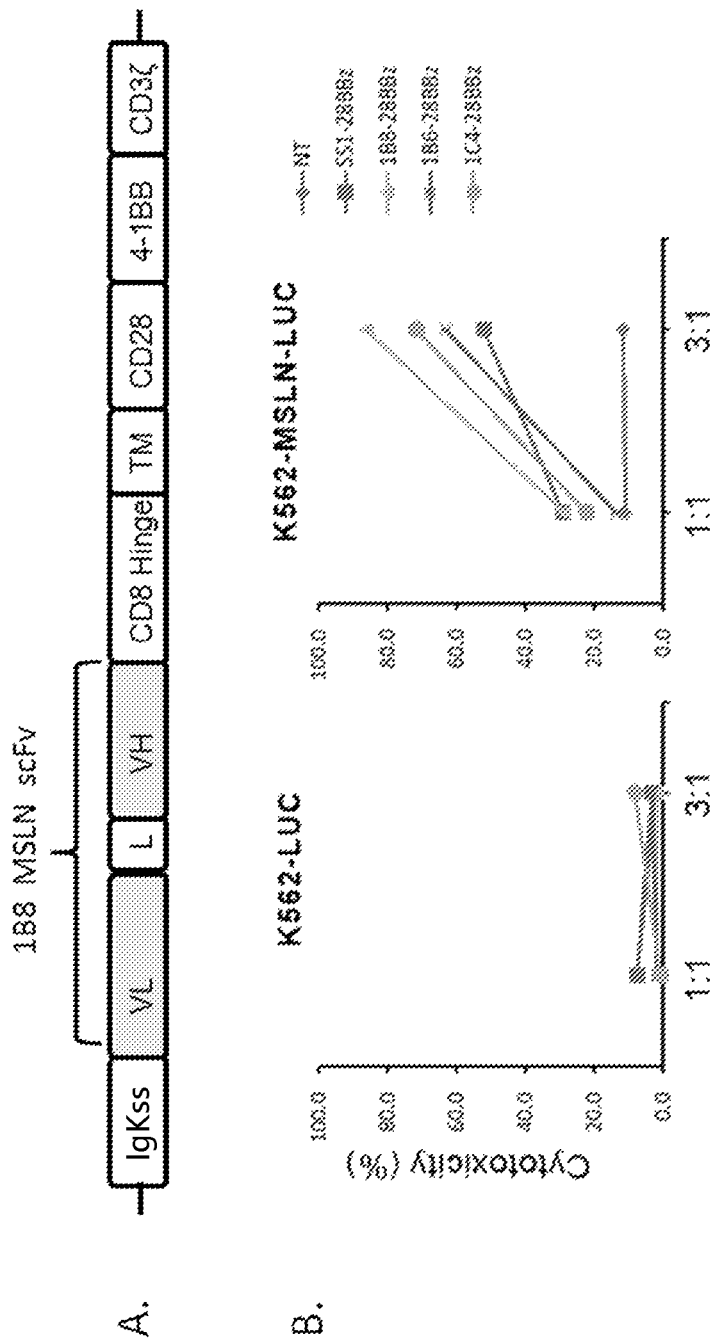
FIG. 8 shows the sequence structure of MSLN CAR and the killing assay results of MSLN CAR-T cells against target cells.

CAR-T cytotoxicity test evaluated the in vitro function of CAR-T cells by detecting the killing effect of the CAR-T cells on target cells thereof in vitro. T cells were co-cultured with K562-LUC-GFP target cells and K562-MSLN-LUC-GFP target cells respectively at different effector-target ratios (when $3 \times 10^4$ target cells were taken as the benchmark, the number of effector cells was the same as the target cells or three times the number of the target cells, respectively). At the same time, a negative control group (NT) was set in which the target cells were mixed with T cells that were not transfected with CAR elements. After 18 hours, luciferase reaction substrate was added into the culture system to detect the fluorescence value, and the killing efficiency was calculated by the following formula: killing efficiency=(1−fluorescence value of the experimental well/fluorescence value of the control well)×100%. The experimental grouping and analysis results were shown in FIG. 8.

The above results showed that the MSLN-targeting CAR-T cells provided in the present invention had stronger immune function than the control SS1, which was characterized by higher secretion level of IFN-γ, higher expression level of CD107a and stronger cytotoxic function against target cells.

The invention claimed is:

1. An antibody or antigen binding fragment thereof specifically binding to human MSLN, which comprises a heavy chain variable domain and a light chain variable domain, wherein the heavy chain variable domain and the light chain variable domain comprise: heavy chain CDR1 as shown in SEQ ID NO: 7, heavy chain CDR2 as shown in SEQ ID NO: 8, and heavy chain CDR3 as shown in SEQ ID NO: 9; and light chain CDR1 as shown in SEQ ID NO: 10, light chain CDR2 as shown in SEQ ID NO: 11, and light chain CDR3 shown in SEQ ID NO: 12.

2. The antibody or antigen binding fragment thereof of claim 1 characterized in that, it is an scFv antibody fragment or a complete IgG1 antibody, and it comprises the heavy chain variable domain as shown in SEQ ID NO: 44 and the light chain variable domain as shown in SEQ ID NO: 45.

3. The antibody or antigen binding fragment thereof of claim 1 characterized in that, it is mouse-derived, chimeric or humanized.

4. The antibody or antigen binding fragment thereof of claim 1 characterized in that, it specifically binds to the extracellular domain of human MSLN.

5. A host cell expressing the antibody or antigen binding fragment thereof of claim 1.

6. The host cell of claim 5 characterized in that, it is a prokaryotic or a eukaryotic cell; preferably, an *Escherichia coli* cell or a Chinese hamster ovary cell.

7. A method of generating an antibody or antigen binding fragment thereof, which comprises culturing the host cell of claim 5 under the condition that the antibody or antigen binding fragment thereof is expressed.

8. A pharmaceutical composition comprising the antibody or antigen binding fragment thereof of claim 1 and one or more pharmaceutically acceptable carriers.

9. An anti-human MSLN chimeric antigen receptor, which comprises an extracellular region, a transmembrane region and an intracellular region, wherein the extracellular region comprises an antigen binding region, and the antigen binding region comprises a heavy chain variable domain and a light chain variable domain, wherein the heavy chain variable domain and the light chain variable domain comprise: heavy chain CDR1 as shown in SEQ ID NO: 7, heavy chain CDR2 as shown in SEQ ID NO: 8, and heavy chain CDR3 as shown in SEQ ID NO: 9; and light chain CDR1 as shown in SEQ ID NO: 10, light chain CDR2 as shown in SEQ ID NO: 11, and light chain CDR3 shown in SEQ ID NO: 12.

10. The chimeric antigen receptor of claim 9, wherein the antigen binding region is an scFv antibody fragment and comprises the heavy chain variable domain as shown in SEQ ID NO: 44 and the light chain variable domain as shown in SEQ ID NO: 45.

11. The chimeric antigen receptor of claim 9 wherein the extracellular region comprises a hinge region, and the hinge region comprises a human CD8α hinge region having an amino acid sequence as shown in SEQ ID NO: 29.

12. The chimeric antigen receptor of claim 9, wherein the transmembrane region comprises a human CD8α transmembrane region having an amino acid sequence as shown in SEQ ID NO: 31.

13. The chimeric antigen receptor of claim 9, wherein the intracellular region comprises a human CD3ζ intracellular region and further comprises a human CD28 intracellular region and/or a human 41BB intracellular region, and the human CD3ζ intracellular region has an amino acid sequence as shown in SEQ ID NO: 37, the human CD28 intracellular region has an amino acid sequence as shown in SEQ ID NO: 33 and/or the human 41BB intracellular region has an amino acid sequence as shown in SEQ ID NO: 35.

14. A modified immune effector cell, which expresses the chimeric antigen receptor of claim 9.

15. The modified immune effector cell of claim 14 characterized in that, it is selected from a T lymphocyte, a NK cell, the immune cell cultured and differentiated from a multipotential stem cell or an embryonic stem cell; preferably a T lymphocyte.

16. A method of modifying an immune effector cell, which comprises modifying the immune effector cell to express the chimeric antigen receptor of claim 9, wherein the immune effector cell is a T lymphocyte.

17. A method of treating a cancer and/or stimulating immune function in a patient with a cancer, comprising administering to the patient a therapeutically effective amount of an antibody or antigen binding fragment thereof specifically binding to human MSLN, an anti-human MSLN chimeric antigen receptor, or a modified immune effector cell,
  wherein the antibody or antigen binding fragment thereof comprises a heavy chain variable domain and a light chain variable domain, wherein the heavy chain variable domain and the light chain variable domain comprise: heavy chain CDR1 as shown in SEQ ID NO: 7, heavy chain CDR2 as shown in SEQ ID NO: 8, and heavy chain CDR3 as shown in SEQ ID NO: 9; and light chain CDR1 as shown in SEQ ID NO: 10, light chain CDR2 as shown in SEQ ID NO: 11, and light chain CDR3 shown in SEQ ID NO: 12,
  the anti-human MSLN chimeric antigen receptor, comprises an extracellular region, a transmembrane region and an intracellular region, wherein the extracellular region comprises an antigen binding region, and the antigen binding region comprises a heavy chain variable domain and a light chain variable domain, wherein the heavy chain variable domain and the light chain variable domain comprise: heavy chain CDR1 as shown in SEQ ID NO: 7, heavy chain CDR2 as shown in SEQ ID NO: 8, and heavy chain CDR3 as shown in SEQ ID NO: 9; and light chain CDR1 as shown in SEQ ID NO: 10, light chain CDR2 as shown in SEQ ID NO: 11, and light chain CDR3 shown in SEQ ID NO: 12, and
  the modified immune effector cell expresses the anti-human MSLN chimeric antigen receptor.

18. The method of claim 17, wherein the cancer is an MSLN positive cancer including mesothelioma, pancreatic cancer or ovarian cancer.

* * * * *

SEQUENCE LISTING

```
<160> NUMBER OF SEQ ID NOS: 47

<210> SEQ ID NO 1
<211> LENGTH: 8
<212> TYPE: PRT
<213> ORGANISM: Homo sapiens

<400> SEQUENCE: 1

Gly Tyr Thr Phe Thr Glu Tyr Thr
1               5

<210> SEQ ID NO 2
<211> LENGTH: 8
<212> TYPE: PRT
<213> ORGANISM: Homo sapiens

<400> SEQUENCE: 2

Ile Asn Pro Tyr Asn Gly Gly Thr
1               5

<210> SEQ ID NO 3
<211> LENGTH: 12
<212> TYPE: PRT
<213> ORGANISM: Homo sapiens

<400> SEQUENCE: 3

Ala Arg Arg Gly Tyr Asp Asn Glu Gly Phe Asp Tyr
1               5                   10

<210> SEQ ID NO 4
<211> LENGTH: 5
<212> TYPE: PRT
<213> ORGANISM: Homo sapiens

<400> SEQUENCE: 4
```

Ser Ser Ile Ser Tyr
1               5

<210> SEQ ID NO 5
<211> LENGTH: 3
<212> TYPE: PRT
<213> ORGANISM: Homo sapiens

<400> SEQUENCE: 5

Asp Thr Ser
1

<210> SEQ ID NO 6
<211> LENGTH: 9
<212> TYPE: PRT
<213> ORGANISM: Homo sapiens

<400> SEQUENCE: 6

Gln Gln Trp Ser Ser Tyr Pro Pro Thr
1               5

<210> SEQ ID NO 7
<211> LENGTH: 8
<212> TYPE: PRT
<213> ORGANISM: Homo sapiens

<400> SEQUENCE: 7

Gly Phe Asn Ile Lys Asp Thr Tyr
1               5

<210> SEQ ID NO 8
<211> LENGTH: 8
<212> TYPE: PRT
<213> ORGANISM: Homo sapiens

<400> SEQUENCE: 8

Ile Asp Pro Ala Asn Gly Asn Thr
1               5

<210> SEQ ID NO 9
<211> LENGTH: 9
<212> TYPE: PRT
<213> ORGANISM: Homo sapiens

<400> SEQUENCE: 9

Ala Arg Asp Gly Trp Tyr Ile Asp Phe
1               5

<210> SEQ ID NO 10
<211> LENGTH: 12
<212> TYPE: PRT
<213> ORGANISM: Homo sapiens

<400> SEQUENCE: 10

Gln Ser Leu Leu Tyr Ser Ser Asn Gln Lys Asn Tyr
1               5                   10

<210> SEQ ID NO 11
<211> LENGTH: 3
<212> TYPE: PRT
<213> ORGANISM: Homo sapiens

<400> SEQUENCE: 11

Trp Ala Ser
1

```
<210> SEQ ID NO 12
<211> LENGTH: 9
<212> TYPE: PRT
<213> ORGANISM: Homo sapiens

<400> SEQUENCE: 12

Leu Gln Tyr Ala Ser Tyr Pro Arg Thr
1               5

<210> SEQ ID NO 13
<211> LENGTH: 9
<212> TYPE: PRT
<213> ORGANISM: Homo sapiens

<400> SEQUENCE: 13

Gly Tyr Ser Ile Thr Ser Asp Tyr Ala
1               5

<210> SEQ ID NO 14
<211> LENGTH: 7
<212> TYPE: PRT
<213> ORGANISM: Homo sapiens

<400> SEQUENCE: 14

Ile Ser Tyr Ser Gly Ser Thr
1               5

<210> SEQ ID NO 15
<211> LENGTH: 13
<212> TYPE: PRT
<213> ORGANISM: Homo sapiens

<400> SEQUENCE: 15

Ala Arg Leu Ala Ser Lys Leu Tyr Trp Tyr Phe Tyr Val
1               5                   10

<210> SEQ ID NO 16
<211> LENGTH: 5
<212> TYPE: PRT
<213> ORGANISM: Homo sapiens

<400> SEQUENCE: 16

Ser Ser Val Ser Tyr
1               5

<210> SEQ ID NO 17
<211> LENGTH: 3
<212> TYPE: PRT
<213> ORGANISM: Homo sapiens

<400> SEQUENCE: 17

Asp Thr Ser
1

<210> SEQ ID NO 18
<211> LENGTH: 9
<212> TYPE: PRT
<213> ORGANISM: Homo sapiens

<400> SEQUENCE: 18

Gln Gln Trp Ser Ser Tyr Pro Pro Thr
1               5
```

```
<210> SEQ ID NO 19
<211> LENGTH: 241
<212> TYPE: PRT
<213> ORGANISM: Homo sapiens

<400> SEQUENCE: 19

Asp Val Val Leu Thr Gln Ser Pro Ala Ile Met Ser Ala Ser Pro Gly
1               5                   10                  15

Glu Lys Val Thr Met Thr Cys Ser Ala Ser Ser Ile Ser Tyr Met
            20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Met Lys Arg Gly Gly Gly Gly Ser
            100                 105                 110

Gly Gly Gly Gly Ser Gly Gly Gly Ser Glu Val His Leu Gln Gln
            115                 120                 125

Ser Gly Pro Glu Leu Val Lys Pro Gly Ala Ser Val Lys Ile Ser Cys
130                 135                 140

Lys Thr Ser Gly Tyr Thr Phe Thr Glu Tyr Thr Met His Trp Val Lys
145                 150                 155                 160

Gln Ser His Gly Lys Ser Leu Glu Trp Ile Gly Leu Ile Asn Pro Tyr
                165                 170                 175

Asn Gly Gly Thr Ser Tyr Asn Gln Lys Phe Lys Gly Lys Ala Thr Leu
            180                 185                 190

Thr Val Asp Lys Ser Ser Ser Thr Ala Tyr Met Glu Leu Leu Ser Leu
        195                 200                 205

Thr Ser Glu Asp Ser Ala Val Tyr Tyr Cys Ala Arg Arg Gly Tyr Asp
    210                 215                 220

Asn Glu Gly Phe Asp Tyr Trp Gly Gln Gly Thr Thr Leu Thr Val Ser
225                 230                 235                 240

Ser

<210> SEQ ID NO 20
<211> LENGTH: 723
<212> TYPE: DNA
<213> ORGANISM: Homo sapiens

<400> SEQUENCE: 20
gatgttgtgc tgacccagtc tccagcaatc atgtctgcat ctccagggga gaaggtcacc      60
atgacctgca gtgccagctc aagtataagt tacatgtact ggtaccagca gaagccagga    120
tcctccccca gactcctgat ttatgacaca tccaacctgg cttctggagt ccctgttcgc    180
ttcagtggca gtgggtctgg gacctcttac tctctcacaa tcagccgaat ggaggctgaa    240
gatgctgcca cttattactg ccagcagtgg agtagttacc cacccacgtt cggaggggg     300 accaagctgg aaatgaaacg cggtggtggt ggttctggcg gcggcggctc cggtggtggt    360
ggatccgagg ttcacctgca acagtctgga cctgagctgg tgaagcctgg ggcttcagtg    420
aagatatcct gcaagacttc tggatacaca ttcactgaat acaccatgca ctgggtgaag    480
cagagccatg gaaagagcct tgagtggatt ggacttatta atccttacaa tggtggtact    540
```

```
agctacaaac agaagttcaa gggcaaggcc acattaactg tagacaagtc atccagcaca      600
gcctacatgg agctcctcag tctgacatct gaggactctg cagtctatta ctgtgcaaga      660
agaggttacg acaacgaagg ctttgactac tggggccaag gcaccactct cacagtctcc      720
tca                                                                    723
```

```
<210> SEQ ID NO 21
<211> LENGTH: 245
<212> TYPE: PRT
<213> ORGANISM: Homo sapiens

<400> SEQUENCE: 21
```

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Glu Ser Glu Asp Phe Ala Asp Tyr Tyr Cys Leu Gln
                85                  90                  95

Tyr Ala Ser Tyr Pro Arg Thr Phe Gly Gly Gly Thr Lys Leu Glu Met
            100                 105                 110

Lys Arg Gly Gly Gly Gly Ser Gly Gly Gly Gly Ser Gly Gly Gly Gly
        115                 120                 125

Ser Glu Val Arg Leu Gln Gln Ser Gly Ala Glu Leu Val Lys Pro Gly
    130                 135                 140

Ala Ser Val Lys Leu Ser Cys Thr Ala Ser Gly Phe Asn Ile Lys Asp
145                 150                 155                 160

Thr Tyr Met His Trp Val Lys Gln Arg Pro Glu Gln Gly Leu Glu Trp
                165                 170                 175

Ile Gly Arg Ile Asp Pro Ala Asn Gly Asn Thr Lys Tyr Asp Pro Lys
            180                 185                 190

Phe Gln Gly Lys Ala Thr Ile Thr Ala Asp Thr Ser Ser Asn Thr Ala
        195                 200                 205

Tyr Leu Gln Leu Ser Ser Leu Thr Ser Glu Asp Thr Ala Val Tyr Tyr
    210                 215                 220

Cys Ala Arg Asp Gly Trp Tyr Ile Asp Phe Trp Gly Gln Gly Thr Thr
225                 230                 235                 240

Leu Thr Val Ser Ser
                245

```
<210> SEQ ID NO 22
<211> LENGTH: 735
<212> TYPE: DNA
<213> ORGANISM: Homo sapiens

<400> SEQUENCE: 22
gacattgtga tgtcacagtc tccatcctcc ctagctgtgt cagttggaga gaaggttact      60
atgagctgca agtccagtca gagccttta tatagtagca atcaaaagaa ctacttggcc      120
tggtaccagc agaaaccagg gcagtctcct aaactgctga tttactgggc atccactagg      180
```

```
gaatctgggg tccctgatcg cttcacaggc agtggatctg ggacagattt cactctcacc    240
atcagcagcc ttgagtctga agattttgca gactattact gtctacaata tgctagttat    300
cctcggacgt tcggtggagg caccaagctg gaaatgaaac gcggtggtgg tggttctggc    360
ggcggcggct ccgtggtggg tggatccgag gttcgcctgc aacagtctgg ggcagagctt    420
gtgaagccag gggcctcagt caagttgtcc tgcacagctt cgggcttcaa cattaaagac    480
acctatatgc actgggtgaa gcagaggcct gaacagggcc tggaatggat tggaaggatt    540
gatcctgcga atggtaatac taaatatgac ccgaagttcc agggcaaggc cactataacg    600
gcagacacat cctccaacac agcctacctg cagctcagca gcctgacatc tgaggacact    660
gccgtctatt actgtgctag agatggttgg tatattgact tctggggcca aggcaccact    720
ctcacagtct cctca                                                      735
```

```
<210> SEQ ID NO 23
<211> LENGTH: 242
<212> TYPE: PRT
<213> ORGANISM: Homo sapiens

<400> SEQUENCE: 23

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Thr Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Asn Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Met Lys Arg Gly Gly Gly Gly Ser
            100                 105                 110

Gly Gly Gly Gly Ser Gly Gly Gly Ser Glu Val Gln Leu Gln Gln
        115                 120                 125

Ser Gly Pro Gly Leu Val Lys Pro Ser Gln Ser Leu Ser Leu Thr Cys
    130                 135                 140

Thr Val Thr Gly Tyr Ser Ile Thr Ser Asp Tyr Ala Trp Asn Trp Ile
145                 150                 155                 160

Arg Gln Phe Pro Gly Asn Lys Leu Glu Trp Met Gly Tyr Ile Ser Tyr
                165                 170                 175

Ser Gly Ser Thr Val Tyr Asn Pro Ser Leu Lys Ser Arg Ile Ser Ile
            180                 185                 190

Thr Arg Asp Thr Ser Lys Asn Gln Phe Phe Leu Gln Leu Asn Ser Val
        195                 200                 205

Thr Thr Glu Asp Thr Ala Thr Tyr Tyr Cys Ala Arg Leu Ala Ser Lys
    210                 215                 220

Leu Tyr Trp Tyr Phe Tyr Val Trp Gly Ala Trp Thr Thr Val Thr Val
225                 230                 235                 240

Ser Ser

<210> SEQ ID NO 24
<211> LENGTH: 726
<212> TYPE: DNA
```

<213> ORGANISM: Homo sapiens

<400> SEQUENCE: 24

```
gacattgtga tgacccagtc tccagcaatc atgtctgcat ctccagggga gaaggtcacc      60
atgacctgca gtgccagctc aagtgtaagt tacatgtact ggtaccagca gaagccaggc     120
acctccccca gactcctgat ttatgacaca tccaacctgg cttctggagt ccctgttcgc     180
ttcagtggca gtgggtctgg gacctcttac tctctcacaa tcaaccgaat ggaggctgaa     240
gatgctgcca cttattactg ccagcagtgg agtagttacc acccacgtt  cggaggggggg    300
accaagctgg aaatgaaacg cggtggtggt ggttctggcg gcggcggctc cggtggtggt     360
ggatccgagg tgcagcttca gcaatcggga cctggcctgg tgaaaccttc tcagtctctg     420
tccctcacct gcactgtcac tggctactca atcaccagtg attatgcctg gaactggatc     480
cggcagtttc caggaaacaa actggagtgg atgggctaca taagctacag tggtagcact     540
gtctacaacc catctctcaa aagtcgaatc tctatcactc gagacacatc caagaaccag     600
ttcttcctgc agttgaattc tgtgactact gaggacacag ccacatatta ctgtgcaaga     660
ttggcttcta agctttactg gtacttctat gtctggggcg catggaccac ggtcaccgtc     720
tcctca                                                                726
```

<210> SEQ ID NO 25
<211> LENGTH: 237
<212> TYPE: PRT
<213> ORGANISM: Homo sapiens

<400> SEQUENCE: 25

```
Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Cys Gly Thr Lys Leu Glu Ile Lys Gly Gly Gly Ser Gly Gly
            100                 105                 110

Gly Ser Gly Gly Gly Ser Gln Val Gln Leu Gln Gln Ser Gly Pro Glu
        115                 120                 125

Leu Glu Lys Pro Gly Ala Ser Val Lys Ile Ser Cys Lys Ala Ser Gly
    130                 135                 140

Tyr Ser Phe Thr Gly Tyr Thr Met Asn Trp Val Lys Gln Ser His Gly
145                 150                 155                 160

Lys Cys Leu Glu Trp Ile Gly Leu Ile Thr Pro Tyr Asn Gly Ala Ser
                165                 170                 175

Ser Tyr Asn Gln Lys Phe Arg Gly Lys Ala Thr Leu Thr Val Asp Lys
            180                 185                 190

Ser Ser Ser Thr Ala Tyr Met Asp Leu Leu Ser Leu Thr Ser Glu Asp
        195                 200                 205

Ser Ala Val Tyr Phe Cys Ala Arg Gly Gly Tyr Asp Gly Arg Gly Phe
    210                 215                 220
```

Asp Tyr Trp Gly Gln Gly Thr Thr Val Thr Val Ser Ser
225                 230                 235

<210> SEQ ID NO 26
<211> LENGTH: 711
<212> TYPE: DNA
<213> ORGANISM: Homo sapiens

<400> SEQUENCE: 26
gatatagagc tcacccagag tcccgcaatc atgtcagcct ctcccggcga aaaagtgacc      60
atgacctgta gtgcttccag ttctgttagt tatatgcact ggtatcaaca gaagtccggg    120
acaagtccta aacgctggat ttatgacact tccaaactgg cttctggagt gcctggcgg    180 ttcagcggga gcggttccgg taactcttac agcctgacca tctcttcagt cgaagctgaa    240
gacgatgcca cgtattattg ccagcaatgg agtaagcacc cactgacatt tgggtgcggg    300
accaagcttg aaataaaggg tggcggcagc ggggcggaa gcggcggggg aagccaggtg    360
caacttcagc aatcaggtcc cgagttggaa aagccgggag ccagcgttaa gatctcatgc    420
aaagctagcg gctactcttt cacaggatat accatgaatt gggtcaagca aagccatgga    480
aaatgtttgg aatggatcgg actgattacc ccctacaacg gggccagctc ctacaatcag    540
aaatttaggg gtaaggccac tctcacagtg gataaaagct caagtactgc ctatatggac    600
ctgcttagtc tgacctcaga ggatagtgcc gtgtactttt gtgccagagg cggttacgac    660
gggcgagggt ttgactactg ggggcagggg acgacggtta ctgtgtctag t              711

<210> SEQ ID NO 27
<211> LENGTH: 22
<212> TYPE: PRT
<213> ORGANISM: Homo sapiens

<400> SEQUENCE: 27

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 28
<211> LENGTH: 66
<212> TYPE: DNA
<213> ORGANISM: Homo sapiens

<400> SEQUENCE: 28
atggacttcc aggtgcagat ttttagtttt cttttgatct ccgccagcgt gataatgtca       60
cgagga                                                                  66

<210> SEQ ID NO 29
<211> LENGTH: 47
<212> TYPE: PRT
<213> ORGANISM: Homo sapiens

<400> SEQUENCE: 29

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 30
<211> LENGTH: 141
<212> TYPE: DNA
<213> ORGANISM: Homo sapiens

<400> SEQUENCE: 30
actacaactc cagcacccag accccctaca cctgctccaa ctatcgcaag tcagcccctg    60
tcactgcgcc ctgaagcctg tcgccctgct gccgggggag ctgtgcatac tcggggactg   120
gactttgcct gtgatatcta c                                             141

<210> SEQ ID NO 31
<211> LENGTH: 22
<212> TYPE: PRT
<213> ORGANISM: Homo sapiens

<400> SEQUENCE: 31

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 32
<211> LENGTH: 66
<212> TYPE: DNA
<213> ORGANISM: Homo sapiens

<400> SEQUENCE: 32
atctgggcgc ccttggccgg gacttgtggg gtccttctcc tgtcactggt tatcacccrtt   60 tactgc                                                               66

<210> SEQ ID NO 33
<211> LENGTH: 41
<212> TYPE: PRT
<213> ORGANISM: Homo sapiens

<400> SEQUENCE: 33

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 34
<211> LENGTH: 123
<212> TYPE: DNA
<213> ORGANISM: Homo sapiens

<400> SEQUENCE: 34
aggtccaaaa gatctaggct gctgcattct gattacatga acatgacgcc gcgccgccct    60
ggtccaacca gaaagcatta tcagccctat gcaccccta gagactttgc cgcctatcgt   120
tcg                                                                 123

<210> SEQ ID NO 35
<211> LENGTH: 48
<212> TYPE: PRT
<213> ORGANISM: Homo sapiens

<400> SEQUENCE: 35

```
Lys Phe Ser Val Val Lys Arg Gly Arg Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu Arg
            35                  40                  45
```

<210> SEQ ID NO 36
<211> LENGTH: 144
<212> TYPE: DNA
<213> ORGANISM: Homo sapiens

<400> SEQUENCE: 36

```
aagttcagtg tcgtgaagag aggccggaag aagctgctgt acatcttcaa gcagcctttc      60
atgaggcccg tgcagactac ccaggaggaa gatggatgca gctgtagatt ccctgaagag     120
gaggaaggag gctgtgagct gaga                                            144
```

<210> SEQ ID NO 37
<211> LENGTH: 111
<212> TYPE: PRT
<213> ORGANISM: Homo sapiens

<400> SEQUENCE: 37

```
Val Lys Phe Ser Arg Ser Ala Asp Ala Pro Ala Tyr Gln Gln Gly Gln
1               5                   10                  15

Asn Gln Leu Tyr Asn Glu Leu Asn Leu Gly Arg Arg Glu Glu Tyr Asp
            20                  25                  30

Val Leu Asp Lys Arg Arg Gly Arg Asp Pro Glu Met Gly Gly Lys Pro
        35                  40                  45

Arg Arg Lys Asn Pro Gln Glu Gly Leu Tyr Asn Glu Leu Gln Lys Asp
50                  55                  60

Lys Met Ala Glu Ala Tyr Ser Glu Ile Gly Met Lys Gly Glu Arg Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg
            100                 105                 110
```

<210> SEQ ID NO 38
<211> LENGTH: 333
<212> TYPE: DNA
<213> ORGANISM: Homo sapiens

<400> SEQUENCE: 38

```
gtgaagttct cccgaagcgc agatgcccca gcctatcagc agggacagaa tcagctgtac      60
aacgagctga acctgggaag acgggaggaa tacgatgtgc tggacaaaag gcggggcaga     120
gatcctgaga tgggcggcaa accaagacgg aagaaccccc aggaaggtct gtataatgag     180
ctgcagaaag acaagatggc tgaggcctac tcagaaatcg gcatgaaggg cgaaagaagg     240
agaggaaaag gccacgacgg actgtaccag gggctgagta cagcaacaaa agacacctat     300
gacgctctgc acatgcaggc tctgccacca aga                                  333
```

<210> SEQ ID NO 39
<211> LENGTH: 54
<212> TYPE: PRT
<213> ORGANISM: Homo sapiens

<400> SEQUENCE: 39

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala
        50
```

<210> SEQ ID NO 40
<211> LENGTH: 232
<212> TYPE: PRT
<213> ORGANISM: Homo sapiens

<400> SEQUENCE: 40

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Gln Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Leu His Glu Ala Leu His Asn His Tyr Thr Gln Lys
    210                 215                 220

Ser Leu Ser Leu Ser Pro Gly Lys
225                 230
```

<210> SEQ ID NO 41
<211> LENGTH: 20
<212> TYPE: PRT
<213> ORGANISM: Homo sapiens

<400> SEQUENCE: 41

```
Met Glu Thr Asp Thr Leu Leu Leu Trp Val Leu Leu Leu Trp Val Pro
1               5                   10                  15

Gly Ser Thr Gly
            20
```

<210> SEQ ID NO 42
<211> LENGTH: 119
<212> TYPE: PRT
<213> ORGANISM: Homo sapiens

<400> SEQUENCE: 42

Glu Val His Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Leu Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Arg Gly Tyr Asp Asn Glu Gly Phe Asp Tyr Trp Gly Gln Gly
            100                 105                 110

Thr Thr Leu Thr Val Ser Ser
        115

<210> SEQ ID NO 43
<211> LENGTH: 106
<212> TYPE: PRT
<213> ORGANISM: Homo sapiens

<400> SEQUENCE: 43

Asp Val Val Leu Thr Gln Ser Pro Ala Ile Met Ser Ala Ser Pro Gly
1               5                   10                  15

Glu Lys Val Thr Met Thr Cys Ser Ala Ser Ser Ser Ile Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Met Lys
            100                 105

<210> SEQ ID NO 44
<211> LENGTH: 116
<212> TYPE: PRT
<213> ORGANISM: Homo sapiens

<400> SEQUENCE: 44

Glu Val Arg Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

```
Gly Arg Ile Asp Pro Ala Asn Gly Asn Thr Lys Tyr Asp Pro Lys Phe
        50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                     85                  90                  95

Ala Arg Asp Gly Trp Tyr Ile Asp Phe Trp Gly Gln Gly Thr Thr Leu
                100                 105                 110

Thr Val Ser Ser
            115
```

<210> SEQ ID NO 45
<211> LENGTH: 113
<212> TYPE: PRT
<213> ORGANISM: Homo sapiens

<400> SEQUENCE: 45

```
Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Leu Glu Ser Glu Asp Phe Ala Asp Tyr Tyr Cys Leu Gln
                     85                  90                  95

Tyr Ala Ser Tyr Pro Arg Thr Phe Gly Gly Gly Thr Lys Leu Glu Met
                100                 105                 110

Lys
```

<210> SEQ ID NO 46
<211> LENGTH: 120
<212> TYPE: PRT
<213> ORGANISM: Homo sapiens

<400> SEQUENCE: 46

```
Glu Val Gln Leu Gln Gln Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
             35                  40                  45

Met Gly Tyr Ile Ser Tyr Ser Gly Ser Thr Val Tyr Asn Pro Ser Leu
         50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                     85                  90                  95

Ala Arg Leu Ala Ser Lys Leu Tyr Trp Tyr Phe Tyr Val Trp Gly Ala
                100                 105                 110

Trp Thr Thr Val Thr Val Ser Ser
            115                 120
```

```
<210> SEQ ID NO 47
<211> LENGTH: 106
<212> TYPE: PRT
<213> ORGANISM: Homo sapiens

<400> SEQUENCE: 47

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Thr Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Asn Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Met Lys
            100                 105
```